United States Patent
Pollock et al.

(10) Patent No.: US 10,967,097 B1
(45) Date of Patent: Apr. 6, 2021

(54) METHODS OF MAKING CHITOSAN/HYALURONIC ACID HYDROGEL COMPOSITIONS AND COMPOSITIONS MADE THEREFROM

(71) Applicant: Oceanit Laboratories, Inc., Honolulu, HI (US)

(72) Inventors: Jacob Pollock, Honolulu, HI (US); Joanne S. M. Ebesu, Waipahu, HI (US); Dexter Poon, Honolulu, HI (US)

(73) Assignee: Oceanit Laboratories, Inc, Honolulu, HI (US)

(*) Notice: Subject to any disclaimer, the term of this patent is extended or adjusted under 35 U.S.C. 154(b) by 265 days.

(21) Appl. No.: 15/384,309

(22) Filed: Dec. 19, 2016

Related U.S. Application Data

(60) Provisional application No. 62/269,784, filed on Dec. 18, 2015.

(51) Int. Cl.
- *A61K 6/00* (2020.01)
- *A61K 9/51* (2006.01)
- *A61L 27/24* (2006.01)
- *A61L 26/00* (2006.01)

(52) U.S. Cl.
CPC ......... *A61L 26/0023* (2013.01); *A61L 26/008* (2013.01); *A61L 26/0095* (2013.01)

(58) Field of Classification Search
CPC .................................................. A61L 26/0023
See application file for complete search history.

(56) References Cited

U.S. PATENT DOCUMENTS

| | | | | |
|---|---|---|---|---|
| 2005/0271729 | A1* | 12/2005 | Wang | A61K 8/735 424/488 |
| 2012/0208890 | A1* | 8/2012 | Gousse | A61L 27/20 514/626 |
| 2013/0129835 | A1* | 5/2013 | Pollock | A61K 8/042 424/574 |

* cited by examiner

*Primary Examiner* — Sarah Alawadi
(74) *Attorney, Agent, or Firm* — Fresh IP PLC; Cliffford D. Hyra; Aubrey Y. Chen

(57) ABSTRACT

A novel hydrogel wound dressing therapy and methods for making the same. The novel methods comprise forming two biopolymers, chitosan and hyaluronic acid, together into a wound dressing with inherent ability to enhance wound closure. The novel composition of the subject invention comprises cross-linked chitosan/hyaluronic acid hydrogels manufactured according to the methods disclosed having a specific cross-link density that results in a swelling ratio of 20 to 100. Hydrogels manufactured in accordance with the method of the invention dramatically increase healing rates and greatly improves outcomes of wound injuries.

16 Claims, 6 Drawing Sheets

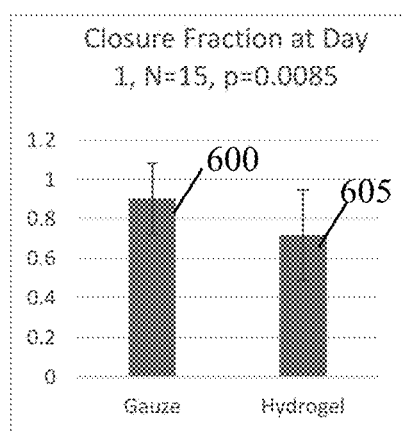 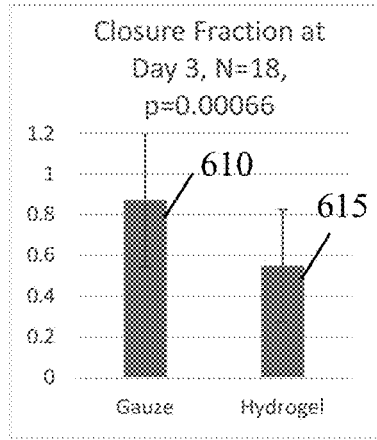 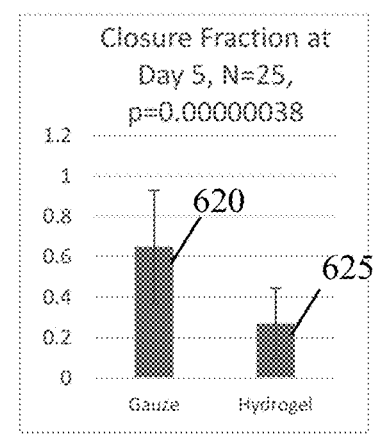
FIG. 6A    FIG. 6B    FIG. 6C
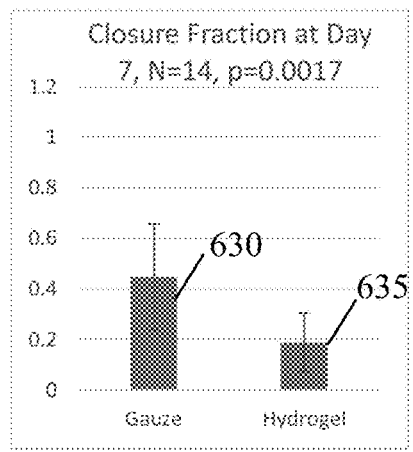 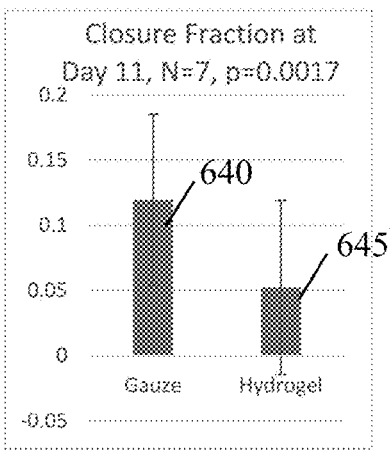
FIG. 6D    FIG. 6E

METHODS OF MAKING CHITOSAN/HYALURONIC ACID HYDROGEL COMPOSITIONS AND COMPOSITIONS MADE THEREFROM

CROSS-REFERENCE TO RELATED APPLICATIONS

This application claims the benefit of U.S. Provisional Application No. 62/269,784, filed Dec. 18, 2015, which is hereby incorporated by reference in its entirety.

STATEMENT REGARDING FEDERALLY SPONSORED RESEARCH OR DEVELOPMENT

This invention was funded in part by the government under U.S. Army Medical Research and Materiel Command contract # W81XWH-11-1-0784. The federal government may have certain rights in the invention.

FIELD OF THE INVENTION

The invention relates to hydrogels and wound treatment. More specifically, this invention describes methods for making chitosan/hyaluronic acid hydrogel compositions and the hydrogel compositions made therefrom useful for promoting tissue growth and wound treatment.

BACKGROUND OF THE INVENTION

Hydrogels consist of three-dimensional hydrophilic polymer structures containing large amounts of water. Because of their unique properties, hydrogels have been used in a variety of pharmaceutical, medical, surgical, and cosmetic applications. Polysaccharide hydrogels can provide favorable microenvironments for cell growth and/or differentiation, making them ideal for wound dressings, cell delivery in regenerative medicine, drug delivery, and other biomedical applications. Hydrogels offer a moist wound healing environment and exudate management. Wounds that are kept moist can have accelerated epithelization, since keratinocytes and epidermal cells can migrate more easily over moist wound surfaces than dry ones. Transparent hydrogels can be used as wound dressings that allow visual wound monitoring without removal of the dressing, which may reduce pain and incidence of infection.

Pollock, J. F. 5 Mar. 2015. US Patent Application no. 20150064147 A1, discloses cross-linked hyaluronic acid-collagen gels and method of making same for improving tissue graft viability and soft tissue augmentation.

Wang W. 26 Jan. 2010. U.S. Pat. No. 7,651,702 B2 discloses methods for crosslinking hyaluronan and chitosanic polymers to create hydrogels that are useful for pharmaceuticals, other medical applications and cosmetics.

Objects of the current invention include new methods for the manufacture of chitosan/hyaluronic acid hydrogel compositions, methods for manufacture of chitosan/hyaluronic acid hydrogel compositions which are more efficient or offer other advantages over the currently known methods of manufacture of chitosan/hyaluronic acid hydrogel compositions, and methods for manufacture of chitosan/hyaluronic acid hydrogel compositions that demonstrate characteristics, such as swelling ratios, that are different from the chitosan/hyaluronic acid hydrogel compositions manufactured though existing methodologies.

SUMMARY OF THE INVENTION

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description. Rather, the scope of the invention is defined by the appended claims.

In certain embodiments, the disclosed embodiments may include one or more of the features described herein.

The above-mentioned and other objects are accomplished through the subject invention, a novel hydrogel wound dressing therapy and methods for making the same that dramatically increases healing rates and greatly improves outcomes of wound injuries. The novel hydrogel wound dressing of the instant invention is more therapeutically effective, requires a lower level of care, and is less expensive than current wound treatments.

The novel methods of the subject invention comprise forming two biopolymers, chitosan and hyaluronic acid (aka hyaluronan), together into a wound dressing with inherent ability to enhance wound closure. Components of the dressing stimulate and modulate immune response, promote cell migration, regulate granulation and re-epithelialization, and prevent growth of microorganisms.

The novel composition of the subject invention in embodiments comprises cross-linked chitosan/hyaluronic acid hydrogels manufactured according to a method disclosed herein having a specific biopolymer composition and cross-link density that results in a swelling ratio of 20 to 100.

Characteristics of hydrogels fabricated according to methods of the subject invention include:
- Optically transparent
- Terminally sterilizable
- Formulated with medical-grade, non-animal products to minimize allergic reaction
- Conforms to wound surface geometry
- Promotes accelerated healing and sealing of damaged tissues to reduce bleeding and risk of microbial infection Pre-clinical trials in a rat full-thickness dermal wound model have demonstrated that embodiments of the invention disclosed herein can achieve levels of healing at day one comparable to moist gauze controls at day five. Within two days of application of the invention, the cut surfaces of the dermal wounds had fully sealed and stopped bleeding, making the dermal tissue more resistant to potential microbial infection. By day four, the wounds treated with the invention were about half the size of wounds treated with moist gauze.

The hydrogels manufactured from the methods described herein can be used in various form factors, including a thin film, membrane or sheet; sponge-type material; powder; in situ forming hydrogel; or extricable gel. Uses include prevention of wound dressing adhesion, as dermal wound dressings or fillers, localized drug delivery vehicles, contact lens-type dressings, tissue graft viability, soft tissue augmentation, hemostatic dressings, or for cell culture or tissue engineering.

A new hydrogel preparation method includes creating a chitosan suspension, adjusting pH of the chitosan suspension to between 4.7 and 7.5, adding buffer salts to the chitosan solution and mixing, combining hyaluronic acid (HA) with second buffer salts and creating an HA solution, adding carbodiimide coupling and activating reagents to the HA solution, adding the chitosan solution to the HA solution, shaking or stirring the resulting mixture, and allowing the resulting mixture to set to form a hydrogel. Creating a chitosan suspension and adjusting pH of the chitosan suspension may comprise preparing an aqueous solution of chitosan in water and adjusting the pH until the solution is clear and adding the first buffer salts to the chitosan solution. In alternative embodiments, chitosan may be added to a buffer salt solution instead of adding buffer salt to a chitosan solution. However, if the buffered solution is at neutral pH, more acid is added to lower the pH to a point at which the chitosan is soluble, which will result in excess salt. If the buffered solution is low pH, the chitosan dissolves immediately, forming clumps and slowing the overall dissolution process. Combining the hyaluronic acid (HA) with the second buffer salts and creating an HA solution may include dissolving HA in a buffer salt solution or adding the second buffer salts to an aqueous solution of HA in water. In alternative embodiments, non-buffer salts or a combination of buffer salts and non-buffer salts may be used in place of the first and/or second buffer salts.

The first and second buffer salts may include a non-coordinating buffer salt and sodium chloride. In embodiments, the first and second buffer salts may include 2-(N-morpholino) ethanesulfonic acid (MES) containing sodium chloride. The MES containing sodium chloride may be between 0.1 M and 1M MES and between 0.9% and 9% wt/vol NaCl in the chitosan and HA solutions. The MES containing sodium chloride may be 0.5 M MES and 4% NaCl in the chitosan solution and 1M MES and 9% NaCl in the HA solution. Concentrations of the first and second buffer salts may differ. The first buffer salt and the second buffer salt may be different.

In embodiments, the carbodiimide coupling and activating reagents may be 1-ethyl-3-(3-dimethylaminopropyl) carbodiimide (EDC) and N-hydroxysulfosuccinimide (NHSS). 50 mM of EDC and 50 mM of NHSS may be added to the HA solution.

In embodiments, the method may also include purifying the hydrogel by dialysis and/or sterilizing the hydrogel by steam in an autoclave. The method may include adjusting pH of the HA solution to between 4.5 and 6.5. The aqueous solution of chitosan in water may be 2% chitosan wt/vol and the HA solution may be 1% HA wt/vol.

A new hydrogel preparation method includes preparing aqueous solutions of 2% chitosan and 1% hyaluronic acid (HA) wt/vol, mixing the aqueous solutions of chitosan and HA, adding buffer salts to the mixture, and adding carbodiimide coupling and activating reagents to the mixture. The buffer salts may include MES and NaCl and the carbodiimide coupling and activating reagents may include EDC and NHSS.

A new hydrogel is prepared according to one of the above methods. A new method of using the new hydrogel includes applying the hydrogel to an open skin wound. The method of use may also include rehydrating the hydrogel prior to applying it to the open skin wound.

These and further and other objects and features of the invention are apparent in the disclosure, which includes the above and ongoing written specification, drawings and claims.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein:

FIGS. 6 A-E are a collection of charts statistically summarizing the healing at different time points of wounds treated with either moist gauze or hydrogel.

DETAILED DESCRIPTION OF PREFERRED EMBODIMENTS

Figure 1:
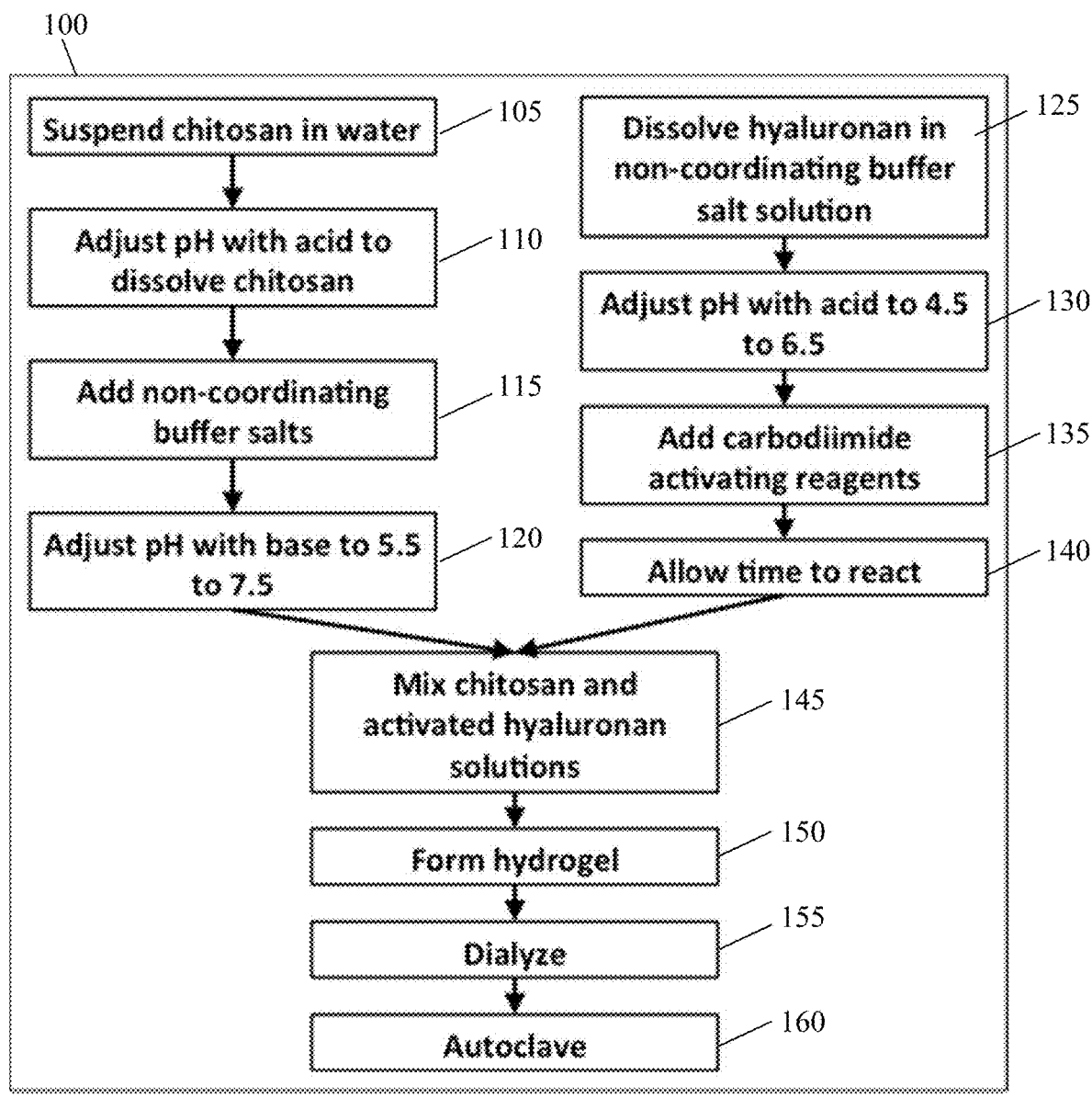
FIG. 1 illustrates in schematic format the steps of synthesis of chitosan/hyaluronic acid hydrogel compositions according to methods of the present invention.

Methods of making chitosan/hyaluronic acid hydrogel compositions and compositions made therefrom will now be disclosed in terms of various exemplary embodiments. This specification discloses one or more embodiments that incorporate features of the invention. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

In the several figures, like reference numerals may be used for like elements having like functions even in different drawings. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail. Any signal arrows in the drawings/figures should be considered only as exemplary, and not limiting, unless otherwise specifically noted.

The description is not to be taken in a limiting sense, but is made merely for the purpose of illustrating the general principles of the invention, since the scope of the invention is best defined by the appended claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items. As used herein, the singular forms "a", "an" and "the" are intended to include the plural forms as well, unless the context clearly indicates otherwise.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

A schematic diagram showing a method 100 of the current invention in generalized format is set forth in FIG. 1. An aqueous suspension of chitosan was prepared 105, the pH was adjusted with acid to dissolve the chitosan 110, non-coordinating buffer salts were dissolved in the solution 115, and the pH was adjusted with base to 5.5 to 7.5 120. Hyaluronan was dissolved in a solution of non-coordinating buffer salts 125 and the pH was adjusted with acid to 4.5 to 6.5 130. Carbodiimide activating reagents were added to the hyaluronan solution 135 and allowed time to react 140. The chitosan and activated hyaluronan solutions were mixed together 145 and the hydrogel was formed 150. The hydrogel was dialyzed 155 to remove excess salts and then autoclaved 160 for steam sterilization.

Figure 2:
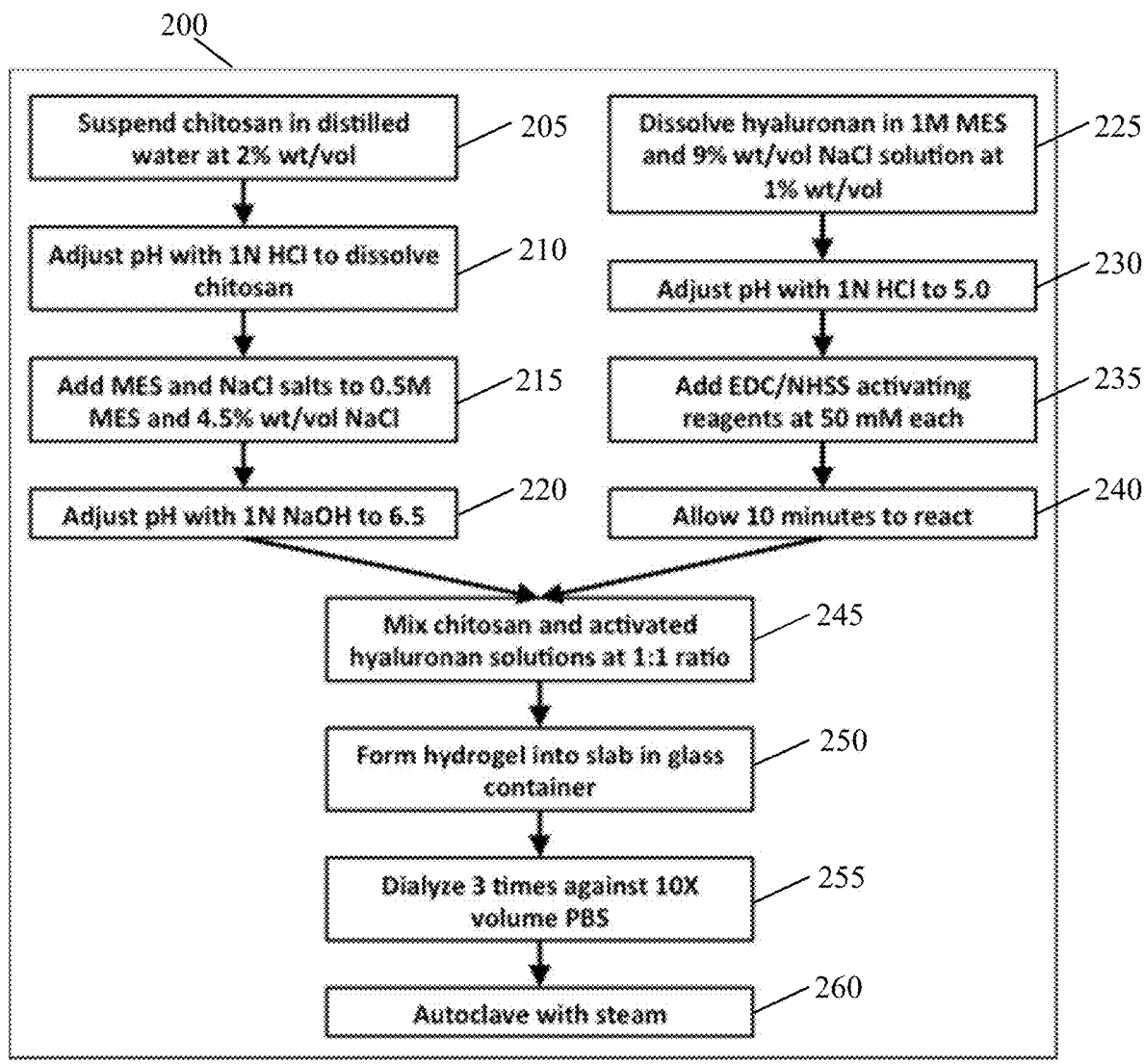
FIG. 2 illustrates in schematic format a more specific embodiment of the method illustrated in FIG. 1.

Depicted in FIG. 2 is a schematic diagram showing a more specific embodiment of a method 200 of the subject invention. An aqueous suspension of chitosan at 2% wt/vol was prepared 205 and the pH was adjusted with 1N HCl to dissolve the chitosan 210. 2-(N-morpholino) ethanesulfonic acid (MES) was dissolved at 0.5M and NaCl was dissolved at 4.5% wt/vol in the chitosan solution 215 and the pH was adjusted with 1N NaOH to 6.5 220. Hyaluronan was dissolved in a solution of 1M MES and 9% wt/vol NaCl at 1% wt/vol 225 and the pH was adjusted with 1N HCl to 5.0 230. 1-Ethyl-3-(3-dimethylaminopropyl) carbodiimide (EDC) and N-hydroxysulfosuccinimide (NHSS) were added at 50 mM each to the hyaluronan solution 235 and allowed to react for 10 minutes 240. The chitosan and activated hyaluronan solutions were mixed together at a 1:1 volume ratio 245 and the hydrogel was formed into a slab in a glass container 250. The hydrogel was dialyzed 3 times against 10× volume phosphate buffered saline (PBS) 255 to remove excess salts and then autoclaved 260 for steam sterilization.

Carbodiimides, such as 1-Ethyl-3-(3-dimethylaminopropyl) carbodiimide (EDC), react with carboxylic acid groups to form an active O-acylisourea intermediate that is easily displaced by nucleophilic attack from primary amino groups. The primary amine forms an amide bond with the original carboxyl group, and a carbodiimide by-product is released as a soluble urea derivative. Carbodiimide reactions are most efficient at acidic (pH 4.5) conditions and must be performed in buffers devoid of extraneous carboxyls and amines, such as 2-(N-morpholino) ethanesulfonic acid (MES). An activating agent, such as a succinimide, such as N-hydroxysuccinimide (NHS), is often included in carbodiimide coupling protocols to improve efficacy or create dry-stable (amine reactive) intermediates. EDC couples NHS to carboxyls, forming an NHS ester that is more stable than the O-acylisourea intermediate while allowing for efficient conjugation to primary amines at physiologic pH.

Chitosan is a linear polysaccharide composed of randomly distributed β-(1-4)-linked D-glucosamine (deacetylated unit) and N-acetyl-D-glucosamine (acetylated unit). Chitosan is hemostatic, biocompatible, bacteriostatic and biodegradable, and accelerates wound healing. It is broken down by lysozyme in the body to glucosamine.

Ultrapure chitosan from a non-animal source is used, preferably in the molecular weight range from 140-220 kilo Daltons (kDa), although chitosan with lower molecular weights (4-140 kDa) or higher molecular weights (220-2000 kDa) or from different sources may be used with less crosslinking and wound healing efficacy.

The term "chitosan" will be understood by those skilled in the art to include all derivatives of chitosan, or deacetylated chitin, or poly-N-acetyl-D-glucosamine, in which most of the N-acetyl groups have been removed by hydrolysis. The chitosan in embodiments has a positive charge.

The chitosan is in embodiments water soluble with a degree of deacetylation between 40% and 98%, and in some such embodiments between 70 and 90%.

Hyaluronic acid is a naturally non-sulfated polysaccharide made of multiple repeating units of N-acetyl-D-glucosamine and D-glucoronic acid. It is an anionic, non-sulfated glycosaminoglycan. It is one of the main components of the extracellular matrix, facilitates cell migration and cell proliferation, and is crucial to the dermal reepithelization process during wound healing.

Hyaluronic acid is a non-sulfated glycosaminoglycan that enhances water retention and resists hydrostatic stresses. It is non-immunogenic and can be chemically modified in numerous fashions. Hyaluronic acid may be anionic at pH ranges around or above the pKa of its carboxylic acid groups. Unless clearly indicated otherwise, reference to hyaluronic acid herein may include its fully protonated, or nonionic form as depicted below, as well as any anionic forms and salts of hyaluronic acid, such as sodium salts, potassium salts, lithium salts, magnesium salts, calcium salts, etc.

Because hyaluronic acid may be anionic and chitosan may be cationic, the two macromolecules may form polyionic complexes in aqueous solution. A polyionic complex may be significantly less soluble in water than either hyaluronic acid or chitosan, and thus may precipitate out of aqueous solution when the two macromolecules are together in a mixture. Furthermore, chitosan is often soluble only at low pH and may precipitate from solution when brought to a pH amenable to carbodiimide coupling.

Under certain conditions, a hyaluronic acid and a chitosan may be combined in an aqueous liquid in which both components are soluble. A hyaluronic acid solution may be activated with a crosslinking reagent at a pH and salt content level that accelerates the activation reaction. The activated hyaluronic acid solution may then be added to and mixed with a chitosan solution to crosslink the two polymers. The pH and salt content of the chitosan solution is controlled to facilitate the reaction and maintain solubility of the two biopolymers. Reaction conditions such as the initial individual and final concentration of hyaluronic acid, the initial individual and final concentration of chitosan, the pH of the solution, and salt concentration may be adjusted to help to prevent polyionic complex formation and facilitate reaction between activated anionic hyaluronic acid and cationic chitosan.

Activated hyaluronic acid and chitosan solutions can react to form a crosslinked macromolecular matrix. Since reaction occurs in an aqueous solution, a crosslinked macromolecular matrix may be dispersed in an aqueous liquid in hydrogel form as it is formed by a crosslinking reaction. A crosslinked macromolecular matrix may be kept in hydrogel form because, in many instances, a crosslinked macromolecular matrix may be used in hydrogel form.

After a crosslinking reaction has occurred, the crosslinked macromolecular matrix may be particulated or homogenized through a mesh. This may help to form an injectable slurry or hydrogel. A mesh used for particulating a crosslinked macromolecular matrix may have any suitable pore size depending upon the size of particles desired. In some embodiments, the mesh may have a pore size of about 10 microns to about 100 microns, about 50 microns to about 70 microns, or about 60 microns.

A hydrogel comprising a crosslinked molecular matrix may be treated by dialysis for purification or other purposes. Dialysis may be carried out by placing a semipermeable membrane between the hydrogel and another liquid so as to allow the hydrogel and the liquid to exchange molecules or salts that can pass through the membrane.

A salt may help to screen the negative charges of hyaluronic acid from the positive charges of chitosan, and may thus prevent precipitation of a polyionic ion complex from solution. However, high concentrations of salt may reduce the solubility of some components in solution. Thus, in some embodiments, the salt concentration of aqueous pre-reaction solutions or a crosslinking reaction mixture may be high enough to screen the charges so that the polyionic ion complex is not formed, but also low enough so that the components of the mixture remain in solution. For example, the total salt concentration of some aqueous pre-reaction solutions or crosslinking reaction mixtures may be about 10 mM to about 1 M, about 100 mM to about 300 mM, or about 150 mM. In some embodiments, a higher salt concentration may increase the efficiency of a crosslinking reaction, which may result in lower swelling and/or higher stiffness.

Some salts in an aqueous pre-reaction solution or a crosslinking reaction mixture may be non-coordinating buffers. Any non-coordinating buffer may be used that is capable of buffering the mixture and does not form coordinating complexes with coupling agents or metal atoms. Examples of suitable non-coordinating buffers may include, but are not limited to, 2-(N-morpholino)ethanesulfonic acid (MES), 3-(N-morpholino)propanesulfonic acid (MOPS), 4-(2-hydroxyethyl)-1-piperazinyl)ethanesulfonic acid (HEPES), 3-[4-(2-hydroxyethyl)-1-piperazinyl]propanesulfonic acid (HEPPS), N-cyclohexyl-2-aminoethanesulfonic acid (CHES), N-cyclohexyl-3-aminopropanesulfonic acid (CAPS), etc.

The concentration of a non-coordinating buffer may vary. For example, some aqueous pre-reaction solutions or crosslinking reaction mixtures may have a buffer concentration in a range of about 10 mM to about 1 M, about 10 mM to about 500 mM, about 20 mM to about 100 mM, or about 25 mM to about 250 mM. Some aqueous pre-reaction solutions or crosslinking reaction mixtures comprise MES at a concentration of about 20 mM to about 1 M, about 20 mM to about 100 mM, about 100 mM, or about 180 mM.

Non-buffering salts may also be included in an aqueous pre-reaction solution or a crosslinking reaction mixture as an alternative to, or in addition, to buffering salts. Some examples may include sodium chloride, potassium chloride, lithium chloride, potassium bromide, sodium bromide, lithium bromide, and the like. The concentration of a non-buffering salt may vary. For example, some mixtures may have a non-buffering salt concentration in a range of about 10 mM to about 1 mM, about 30 mM to about 500 mM, or about 50 mM to about 300 mM. In some embodiments, sodium chloride may be present at a concentration in a range of about 0.5% w/v to about 2%, about 0.9% w/v to about 1.6% w/v, about 20 mM to about 1 M, about 40 mM to about 500 mM, about 50 to 300 mM, about 80 mM to about 330 mM, about 150 mM, or about 270 mM.

Any water-soluble coupling agent may be used that can crosslink hyaluronic acid to chitosan. Some non-limiting examples of a coupling agent include carbodiimides such as N,N'-dicyclohexylcarbodiimide (DCC), N,N'-diisopropylcarbodiimide (DIC), or 1-ethyl-3-(3-dimethylaminopropyl) carbodiimide (EDC), etc. Carbodiimide coupling agents may facilitate ester or amide bond formation without becoming part of the linkage. In other words, an ester bond or an amide bond may comprise atoms from a carboxylate group from one of hyaluronic acid or chitosan, and a hydroxyl group or an amine group from the other. However, other coupling agents that become part of the crosslinking group may be used. The concentration of a coupling agent may vary. In some embodiments, a coupling agent may be present at about 2 mM to about 150 mM, about 2 mM to about 50 mM, about 20 mM to about 100 mM, or about 50 mM. In some embodiments, the coupling agent is EDC that is present at a concentration of about 20 mM to about 100 mM, about 2 mM to about 50 mM, or about 50 mM.

As a result of a crosslinking reaction, a crosslinked macromolecular matrix may comprise a crosslinking component that crosslinks or covalently connects the hyaluronic acid component to the chitosan component. As explained above, a crosslink component comprises a plurality of crosslink units, or individual covalent bonding links, between the hyaluronic acid component and the chitosan component. A crosslink unit may simply be a direct bond between a hyaluronic acid component and a chitosan component, so that the coupling agent may not be incorporated into the crosslinked macromolecular matrix. Alternatively, a crosslink unit may contain additional atoms or groups from the coupling agent such that at least a portion of the coupling agent may become part of the crosslinked macromolecular matrix. At least a portion of the crosslink units comprise an ester bond or an amide bond. In some embodiments, at least a portion of the crosslink units may be —CON— or —CO2—, where the N is a nitrogen from an amino acid residue.

An activating agent may be used to increase the rate of the crosslinking reaction and the number of crosslink units in the final product. In some embodiments, an activating agent may be a triazole such as hydroxybenzotriazole (HOBT) or 1-hydroxy-7-azabenzotriazole (HOAT); a fluorinated phenol such as pentafluorophenol; a succinimide such as N-hydroxysuccinimide (NHS) or N-hydroxysulfosuccinimide (NHSS), and the like.

The concentration of an activating agent may vary. In some embodiments, the activating agent may have a concentration of about 2 mM to about 200 mM, about 2 mM to about 50 mM, about 20 mM to about 100 mM, or about 50 mM. In some embodiments, the activating agent may be NHS or NHSS at a concentration of about 2 mM to about 50 mM. In some embodiments, the activating agent may be N-hydroxysulfosuccinimide, sodium salt, at a concentration of about 20 mM to about 100 mM, or about 50 Mm.

In some embodiments, a crosslinking reaction mixture may comprise a carbodiimide coupling agent and an activating agent. In some embodiments, the coupling agent is EDC and the activating agent is NHS or sulfoNHS. In some embodiments EDC is present at a concentration of about 2 mM to about 50 mM and NHS or sulfoNHS is present at about 2 mM to about 50 mM.

The current invention improves upon and is patentably distinct from the method of Pollock disclosed in US Patent Application no. 20150064147 A1 (hereafter just "Pollock") at least in that the subject invention uses chitosan instead of collagen as the main component that is cross-linked to hyaluronic acid using EDC. Further, embodiments of the current invention are able to be steam sterilized via autoclave instead of with exposure to 70% isopropanol, which is more effective and does not add any potential irritants to the hydrogel. Additionally, there is a difference in the reaction chemistry. According to embodiments of the current invention, hyaluronic acid is activated with EDC/NHS prior to addition to chitosan whereas in Pollock, EDC is introduced as a coupling agent later, at the cross-linking step. See, e.g., Pollock, ¶090.

The current invention improves upon and is patentably distinct from the method of Wang disclosed in U.S. Pat. No. 7,651,702 B2 (hereinafter just "Wang"), at least since according to at least some methods of the present invention, the hyaluronan and chitosan are mixed together after the addition of EDC. Compared with the current invention, the method of Wang creates a solution of chitosan and hyaluronic acid prior to addition of EDC, whereas embodiments of the current invention utilize an activation step in which EDC is added to a solution of hyaluronic acid to activate it and the activated hyaluronic acid solution is added to a solution of chitosan. Furthermore, the method of Wang does not include the addition of NHS to the EDC; when added to EDC, NHS serves as a coupling reagent that forms a highly reactive activated acid intermediate, thus improving the reaction efficiency. In addition, the pH of the chitosan-hyaluronan solution in the method of Wang (2010) is 7.2-7.8, much higher than the optimal pH of 4.5 for EDC reactions. In some embodiments of the current invention, the pH of the hyaluronic acid activating solution is 5.4, greatly enhancing the efficiency of the activation step and overall reaction. The pH of the chitosan solution may be adjusted to 6.5 prior to the addition of the hyaluronic acid-EDC-NHS solution to provide a more acidic environment for the EDC-NHS reaction to occur and further improving the efficiency of the reaction.

Additional improvements of embodiments of the current invention over that of Wang include: use of MES buffer vs water, use of a non-coordinating buffer without amines or carboxylic acid groups enhances the efficiency of the reaction; faster gelation time (30 seconds to 15 minutes vs 30 minutes to 3 hours); use of a terminal sterilization step without compromising gel properties; swelling ratio—the hydrogels of the current invention have much lower swelling ratios in water and buffer than those in the Wang patent, likely due to more efficient cross-linking reaction and higher crosslink density.

The methods disclosed and the efficacy of the hydrogel products produced by the disclosed methods are further illustrated in the experiments described below:

Example 1

Hydrogels were prepared from these high purity, high molecular weight chitosan and hyaluronic acid sources by carbodiimide cross-linking. Due to electrostatic interaction between the cationic chitosan and the anionic hyaluronic acid, the two biopolymers typically precipitate when mixed in solution. The solubility of a binary mixture can be controlled through pH and salt concentration. This is one challenge in creating a transparent, robust hydrogel with cationic and anionic biopolymers.

In one formulation, a 1 weight % solution of hyaluronic acid in 0.1 M 2-(N-morpholino) ethanesulfonic acid (MES) with 0.9 weight % sodium chloride (NaCl) and pH 5.4 and a 2 weight % solution of chitosan in 0.1 M MES with 0.9 weight % NaCl and pH 5.4 were prepared. Cross-linking reagents were added to the hyaluronic acid solution at 50 mM N-hydroxysulfosuccinimide (NHSS) and 50 mM 1-ethyl-3-(3-dimethylaminopropyl) carbodiimide (EDC). After 5 minutes, equal parts of the activated hyaluronic acid solution and chitosan solution were rapidly mixed and poured into a mold. The reaction was allowed to proceed for 30 minutes, after which the hydrogel sample was removed from the mold and washed in excess phosphate buffered saline (PBS). The resulting hydrogel was opaque and shrank slightly when washed in PBS.

In another formulation, a 1 weight % solution of hyaluronic acid in deionized water and 2 weight % solution of chitosan in deionized water were prepared. The two solutions were rapidly mixed in equal parts, resulting in an opaque suspension. Then, MES with NaCl was added to 1 M MES with 9 weight % NaCl in order to clear the solution. Cross-linking reagents were added at 50 mM NHSS and 50 mM EDC concentrations, and the solution was poured into a mold. The reaction was allowed to proceed for 30 minutes, after which the hydrogel sample was removed from the mold and washed in excess phosphate buffered saline (PBS). The resulting hydrogel was clear and shrank slightly when washed in PBS.

Figure 3:
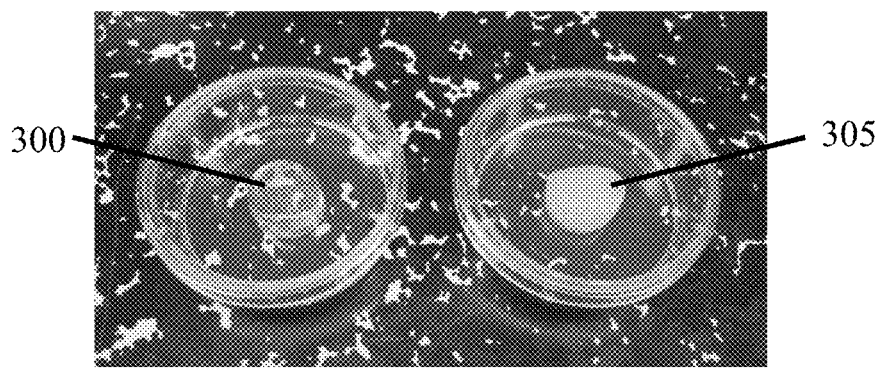
FIG. 3 shows samples of hydrogel produced from chitosan and hyaluronic acid under different conditions.

The 0.1 M MES and 0.9 weight % NaCl resulted in an opaque hydrogel, but the 1 M MES and 9 weight % NaCl resulted in a transparent hydrogel. See FIG. 3 showing hydrogel specimens 305, 300 made with the same chitosan and hyaluronic acid, but produced with 0.1 M MES or 1 M MES, respectively.

Example 2

According to another embodiment of the method of the current invention: Chitosan was dissolved in deionized water at 2% wt/vol. The pH was adjusted with 1 N HCl until the solution was clear, pH=4.7. MES was added at 2.8 g to 30 mL of chitosan solution and sodium chloride was added at 1.2 g to form a 0.5 M MES solution with 4 wt % NaCl. Hyaluronic acid was dissolved in 1 M MES solution with 9 wt % NaCl to make 1% wt/vol hyaluronic acid in MES buffer, pH=5.4. The hyaluronic acid solution was activated by adding 0.03 g EDC and 0.01 g NHSS to 2 mL of the hyaluronic acid solution. The activation step was allowed to proceed for two minutes. The activated hyaluronic acid solution (2 mL) was mixed with 8 mL chitosan solution and quickly poured into a Petri dish. The solution set rapidly into a very clear gel. The gel was washed three times with 2 L of deionized water at 1 hour per wash. The gel was autoclaved in the unwrapped cycle (15 minutes of steam sterilization and 15 minutes of drying).

Example 3

An aqueous solution of 2% chitosan in water (weight/volume) was prepared, and the pH adjusted with 1 N HCl until the solution was clear, pH=5. Next, 2.8 g of 2-(N-morpholino) ethanesulfonic acid (MES) and 1.2 g NaCl was added to 30 mL chitosan solution and the mixture shaken to dissolve the salt. Hyaluronic acid (HA) was dissolved in 1 M MES and 9 wt % NaCl to make a 1% (weight/volume) solution. Cross-linking reagents, N-hydroxysulfosuccinimide (NHSS; 0.01 g) and 1-ethyl-3-(3-dimethylaminopropyl) carbodiimide (EDC; 0.03 g), were added to 2 mL of 1% HA; this mixture was then shaken for about 30 sec to activate the HA. Eight mL of chitosan solution was then added to this mixture, which was shaken to mix and then poured into a 60 mm Petri dish. This formulation resulted in a clear gel that set very quickly. Excess salt was removed from the hydrogel sample by washing it with large volumes (3×2 L) of deion-

Example 4

A further modification of the hydrogel formula is described as follows: Dissolve chitosan at 2% wt/vol (0.8 g chitosan in 40 mL distilled water). Adjust the pH with 1N HCl until solution is clear. Add 5.3 g of MES salt (70% MES/30% NaCl) to 40 mL chitosan solution. Shake to dissolve. Adjust pH from 5.0 to 6.5 with addition of 1 N NaOH. Make a 1% sodium hyaluronate solution by dissolving hyaluronate at 1% wt/vol in 1 M MES and 9 wt % NaCl (0.4 g hyaluronate in 40 mL MES), pH=5.4. Dissolve overnight. Add 0.06 g EDC and 0.02 g sulfoNHS to 10 mL of 1% wt/vol hyaluronate, stir, and incubate for 5 minutes. Add 10 mL of the activated 1% wt/vol hyaluronate solution to 10 mL of 2% wt/vol chitosan, mix, and pour into mold. Allow 15 minutes to set into a clear, firm gel. Dialyze the gel against 4 L of PBS over one hour in a strainer container. Repeat two more times. Autoclave the gels in air in an appropriate container.

Example 5

Briefly, hyaluronic acid solution at 1% wt/vol was activated with 50 mM of EDC and 50 mM of NHSS in 1 M MES and 9 wt % NaCl at pH 5.4. The activated hyaluronic acid solution was added at equal volume to 2% wt/vol chitosan solution in 0.5 M MES and 4.5 wt % NaCl at pH 6. The resulting hydrogels were washed in 10× volume of phosphate buffered saline (PBS) overnight to remove excess salts. 12 mm plugs were excised from the hydrogel slab using a dermal punch and transferred to individual 50 mL beakers and covered with aluminum foil that was previously punctured to allow evaporation. The gels were then autoclaved in the "unwrapped" cycle (20 minutes sterilization and 15 minutes drying). Excess liquid following autoclave was sterilely removed and the gel plugs were placed to partially dry at room temperature for 4 hr, then stored at 4° C. until ready for use. Hydrogels were rehydrated in PBS for at least 15 min before use.

The rat dermal wound healing model protocol is based on Mendes et al (2012), Lee et al (2009) and Galiano et al (2004), with some modifications. Rats were anesthetized via an inhalational anesthetic, 5% isoflurane, in 100% oxygen for induction, followed by 1-3% isoflurane in 100% oxygen for maintenance. Each animal was weighed individually. The dorsal supracostal region of each rat was shaved and disinfected with three alternating washes each of Betadine and 70% isopropyl alcohol. To minimize wound contraction and allow wound healing to occur through the processes of granulation, tissue formation and re-epithelialization, the wounds were splinted following the procedure of Galiano et al (2004). Briefly, the splints were made by punching 8 mm diameter holes using a biopsy punch in the center of a donut-shaped silicone corn pad. Two splints were placed on the dorsum of each animal, on either side of the dorsal midline (FIG. 6a). An immediate-bonding adhesive, Vet-Bond, was used to fix the splint to the skin followed by interrupted 6-0 nylon sutures to ensure position (Galiano et al, 2004). This was repeated for each splint. Using a 5 mm diameter biopsy punch tool, a full-thickness skin incision was made within the center of each splint (FIG. 6b).

Each animal received one sterile treatment for each wound on its dorsum, a gauze dressing wetted with phosphate buffered saline (PBS, pH 7.4) and a hydrogel dressing described above. Placement of the two treatments on each animal was randomly selected. Each type of dressing was cut to approximately 8 mm diameter to fit within the hole in the center of each splint, fully covering the wounds (FIG. 6c). The dressings were covered with a clear window bandage to help keep the treatments moist. The dressings were then loosely covered with a gauze sponge to prevent friction between the window bandage and the rat jacket. The rat jacket was then secured onto the animal using a suture tying the two hooks on its dorsal opening (FIG. 6d). The rat jacket was used to provide a non-occlusive covering of the surgical site and to prevent oral ingestion or removal of the dressings by the animals. Digital photographs were taken on the day of surgery and every day thereafter, with and without a ruler held adjacent to the wound for subsequent normalization of wound sizes. The animals were anesthetized each day in order to change their dressings and to photograph the wounds. The wounds were measured daily in two perpendicular directions (the largest, A, and smallest, B, diameters of the wound) using a caliper or ruler, and the wound areas estimated based on these measurements using the equation to calculate area of an ellipse: Area=$\pi$*A*B. Seven animals per treatment were euthanized on each day of the tissue collection on days 0, 5, 7, 9 and 11. Full thickness skin biopsies were collected using an 8 mm diameter biopsy punch, and then placed into 10% neutral buffered formalin and kept at 4° C. until analyzed.

Figure 4A:
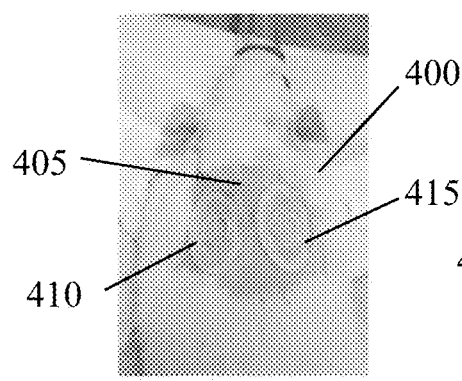
FIGS. 4 A-D illustrate the steps taken in a small animal model of dermal wound healing to demonstrate the accelerated wound healing caused by the inventive hydrogel.
Figure 4B:
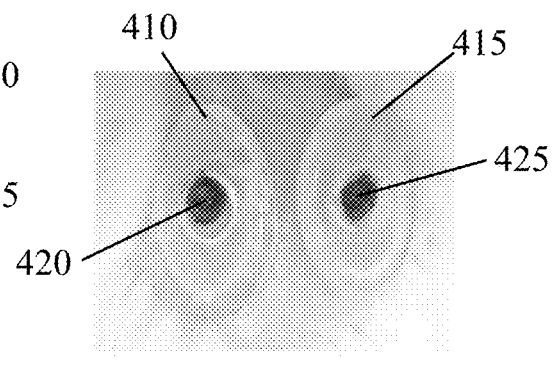
Figure 4C:
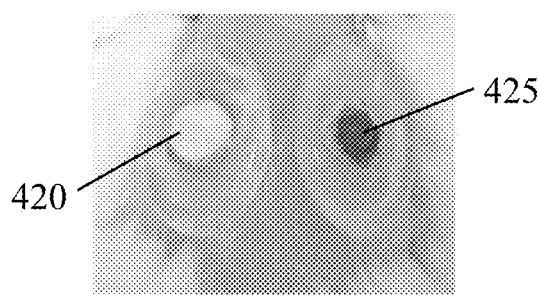
Figure 4D:
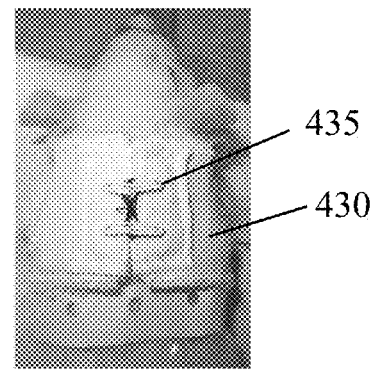

FIG. 4A shows the rat 400 on Day 0 with shaved dorsum 405 and splints 410, 415 attached with VetBond. FIG. 4B shows the rat with 5 mm diameter full-thickness wounds 420, 425 in the center of each splint 410, 415. FIG. 4C shows the wounds with sterile moist gauze 420 and transparent hydrogel 425 treatments. FIG. 4D shows the rat wearing a jacket 430 secured with suture thread 435.

Time to wound closure is defined as the time at which the wound bed is completely filled in with new tissue.

Figure 5:
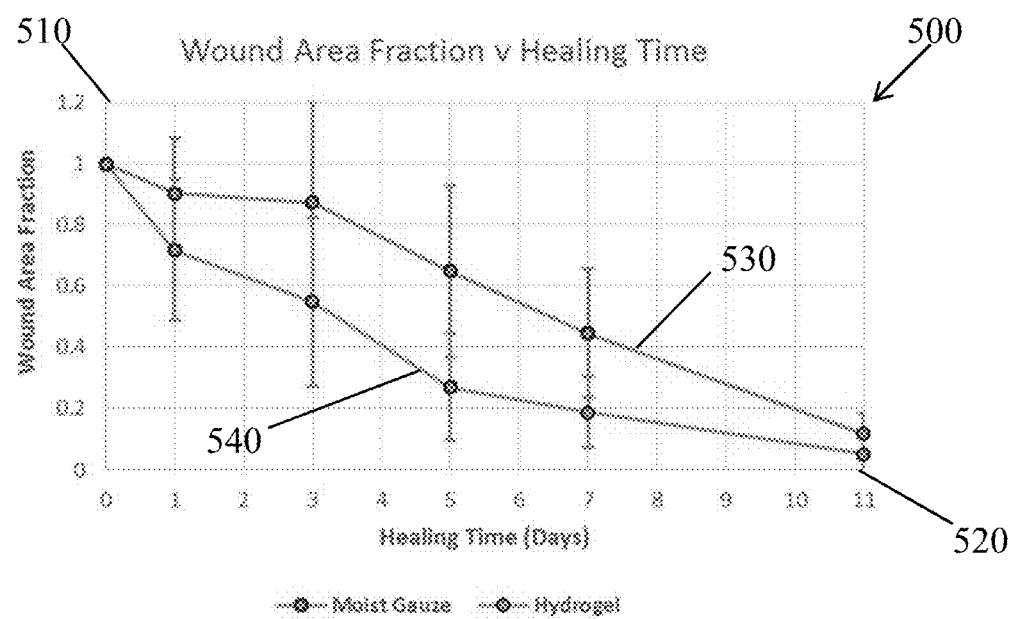
FIG. 5 shows the wound healing rate in the small animal model of dermal wound healing with moist gauze control and the hydrogel of the invention.

Preliminary wound area data based on the daily measurements was calculated as wound area fraction or closure fraction using the equation: Current wound area/Initial wound area. The data is summarized 500 in FIG. 5, with wound area fraction 510 shown on the y-axis and healing item in days 520 on the x-axis, comparing moist gauze 53—with hydrogel 540. The data is shown for individual days comparing the two treatment groups, including P values (all <0.05), in FIG. 6. These results show that the hydrogel significantly (P<0.01) decreased the average wound fraction on all sample days even by Day 1 (FIG. 5).

Illustrated in FIGS. 6A-E is a summary of wound area data expressed as a fraction of the original wound area over time. The two treatment groups are significantly different (P<0.01) on each day except for Day 0.

Separate data expressed as closure fraction for Days 1 (FIG. 6A), 3 (FIG. 6B), 5 (FIG. 6C), 7 (FIG. 6D), and 11 (FIG. 6E) are illustrated, with the significance (P) values shown for each set of data. By Day 3, the wounds treated with hydrogel had significantly (P=0.00066) reduced in size, by almost half (FIG. 6B). This difference was even more pronounced on Day 5 (P=0.00000038, FIG. 6C). FIG. 6A shows that on day 1, the closure fraction for gauze 600 averages around 0.9, and for hydrogel 605 around 0.7. FIG. 6B shows that on day 3, the closure fraction for gauze 610 averages slightly under 0.9, and for hydrogel 615 under 0.6. FIG. 6C shows that on day 5, the closure fraction for gauze 620 averages around 0.6, and for hydrogel 625 under 0.3. FIG. 6D shows that on day 7, the closure fraction for gauze 630 averages over 0.4, and for hydrogel 635 around 0.2.

FIG. 6E shows that on day 11, the closure fraction for gauze 640 averages around 0.12, and for hydrogel 645 around 0.05.

Figure 7:
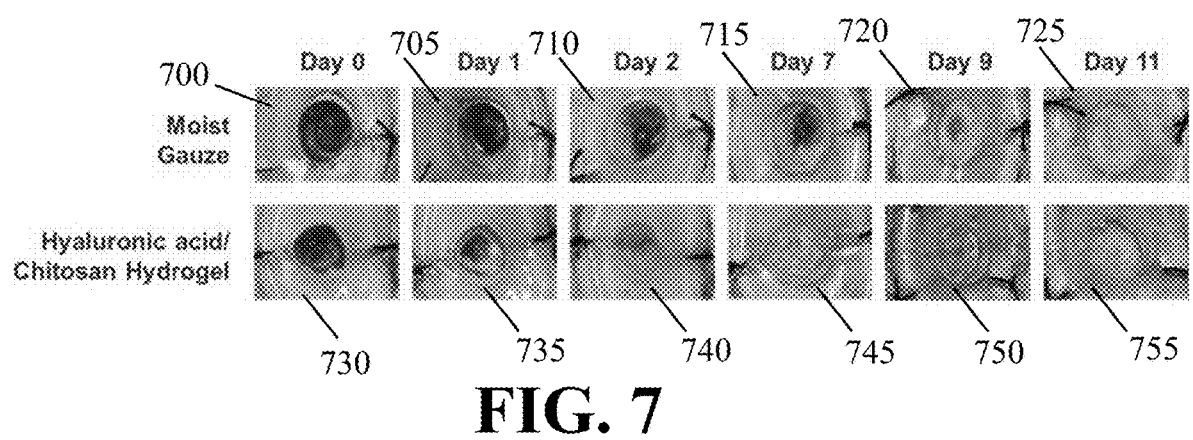
FIG. 7 shows representative photographs of splinted wounds treated with either moist gauze or hydrogel at different time points.

Sequential photos 700-755 of a representative animal treated with both moist gauze and the hydrogel of the instant invention over a period of 11 days are shown in FIG. 7. An important difference observed between the wounds receiving the two treatments is that the wounds receiving hydrogel in all animals, not just the one 730-755 shown in FIG. 7, resolved much quicker than those receiving the moist gauze treatment, e.g. 700-725. Specifically, the surfaces of these wounds stopped bleeding and were covered with pink tissue usually by Day 1, see 735, whereas the wounds treated with moist gauze remained red in color and bleeding usually until Day 7, see 715.

SUMMARY AND SCOPE

Features of embodiments of the hydrogel in this invention include:
Optically transparent
Terminally sterilizable
Formulated with medical-grade, non-animal products to minimize allergic reaction
Conforms to wound surface geometry
Promotes accelerated healing and sealing of damaged tissues to reduce bleeding and risk of microbial infection The hydrogel can be used in various form factors, including a thin film, membrane or sheet; sponge-type material; powder; in situ forming hydrogel; or extricable gel. Uses include prevention of wound dressing adhesion, as dermal wound dressings or fillers, localized drug delivery vehicles, contact lens-type dressings, tissue graft viability, soft tissue augmentation, hemostatic dressings, or for cell culture or tissue engineering.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the," and similar references used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described. The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application.

What is claimed is:
1. A hydrogel preparation method, comprising:
creating a chitosan suspension in water;
adjusting pH of the chitosan suspension to between 4.7 and 7.5 to dissolve the chitosan and form a chitosan solution;
combining first buffer salts with the chitosan solution;
combining hyaluronic acid (HA) and second buffer salts in water and creating an HA solution with a pH of between 4.5 and 6.5;
adding carbodiimide coupling and activating reagents to the HA solution, thereby creating an activated HA solution;
adding the chitosan solution to the activated HA solution to form a resulting mixture; and
allowing the resulting mixture to set to form a hydrogel.
2. A hydrogel preparation method according to claim 1, wherein the first and second buffer salts comprise a non-coordinating buffer salt and sodium chloride.
3. A hydrogel preparation method according to claim 1, wherein the first and second buffer salts comprise 2-(N-morpholino) ethanesulfonic acid (MES) containing sodium chloride.
4. A hydrogel preparation method according to claim 3, wherein the MES containing sodium chloride comprises between 0.05M and 5M MES and between 0.1% and 20% wt/vol NaCl in the chitosan and HA solutions.
5. A hydrogel preparation method according to claim 3, wherein the MES containing sodium chloride comprises 0.5M MES and 4% NaCl in the chitosan solution and 1M MES and 9% NaCl in the HA solution.

6. A hydrogel preparation method according to claim 1, wherein concentrations of the first and second buffer salts are different.

7. A hydrogel preparation method according to claim 1, wherein the first buffer salt and the second buffer salt are different.

8. A hydrogel preparation method according to claim 1, wherein the carbodiimide coupling and activating reagents are 1-ethyl-3-(3-dimethylaminopropyl) carbodiimide (EDC) and N-hydroxysulfosuccinimide (NHSS) or N-hydroxysuccinimide (NHS).

9. A hydrogel preparation method according to claim 8, wherein 10 mM to 100 mM of EDC and 10 mM to 100 mM of NHSS are added to the HA solution.

10. A hydrogel preparation method according to claim 1, further comprising purifying the hydrogel by dialysis.

11. A hydrogel preparation method according to claim 1, further comprising sterilizing the hydrogel by steam in an autoclave.

12. The hydrogel preparation method according to claim 1, wherein the chitosan solution comprises 0.5% to 3% chitosan wt/vol and the HA solution comprises 0.2% to 2% HA wt/vol.

13. A hydrogel preparation method, comprising:
adjusting a suspension of chitosan in water to a pH of between 4.7 to 7.5 to dissolve the chitosan and form an aqueous chitosan solutions comprising 2% chitosan, preparing an aqueous solution of 1% hyaluronic acid (HA) wt/vol;
forming a mixture by mixing the aqueous chitosan solution and the aqueous solution of 1% hyaluronic acid (HA);
adding buffer salts to the mixture; and
adding carbodiimide coupling and activating reagents to the mixture.

14. A hydrogel preparation method according to claim 13, wherein the buffer salts comprise MES and NaCl and the carbodiimide coupling and activating reagents comprise EDC and NHSS.

15. A hydrogel preparation method according to claim 1, wherein the hydrogel has a swelling ratio of between 20 to 100.

16. A hydrogel preparation method according to claim 1, wherein
the resulting mixture is particulated or homogenized through a mesh.

* * * * *